United States Patent [19]

Hou et al.

[11] Patent Number: 5,463,051
[45] Date of Patent: Oct. 31, 1995

[54] PROCESS FOR PREPARING BENZAZEPINE INTERMEDIATES FOR THE SYNTHESIS OF D1 ANTAGONISTS

[75] Inventors: Donald Hou, Verona; Richard W. Draper, North Caldwell; Gary M. Lee, Murray Hill; Janet L. Mas, Scotch Plains, all of N.J.; Ingrid Mergelsberg, Dagmersellen, Switzerland

[73] Assignee: Schering Corporation, Kenilworth, N.J.

[21] Appl. No.: 127,862

[22] Filed: Sep. 27, 1993

[51] Int. Cl.[6] .................... C07D 223/14; C07D 203/26; C07D 405/06

[52] U.S. Cl. .................... 540/576; 548/955; 548/961; 564/308; 564/428

[58] Field of Search .................... 540/576; 548/955, 548/961

[56] References Cited

U.S. PATENT DOCUMENTS 4,973,586  11/1990  Berger et al. .................... 514/217

OTHER PUBLICATIONS

Berger, et al, *J. Med. Chem.*, 32, 1913–1921 (1989).
Crabb, et al, *Mag. Res. in Chem.*, 24, 798–802 (1986).
Lukes, et al, *Coll. Czech. Chem. Comm.*, 25, 492–501 (1960).
Sharpless, et al, *J. Org. Chem.*, 57, 2768–2771 (1992).
Zhang, et al, *J. Org. Chem.*, 56, 2296–2298 (1991).
Gribble, et al, *J. Org. Chem.*, 46, 2433–2434 (1981).
Braun, et al, *Chem Berichte*, 54, 597–618 (1921).
Braun, et al, *Chem Berichte*, 55, 3648–3663 (1922).
Jacobsen, et al, *J. Amer. Chem. Soc.*, 110, 1968–1970 (1988).
Buckley, et al, *J. Amer. Chem. Soc.*, 103, 6157–6163 (1981).
Lee, et al, *Tet. Lett.*, 32, 5055–5058 (1991).
Okada, et al, *Bull. Chem. Soc. Japan*, 43, 1185–1189 (1970).
Imuta, et al, *J. Org. Chem.*, 44, 1351–1352 (1979).

*Primary Examiner*—Philip I. Datlow
*Attorney, Agent, or Firm*—Paul A. Thompson

[57] ABSTRACT

Disclosed are a process and intermediates of the formulae

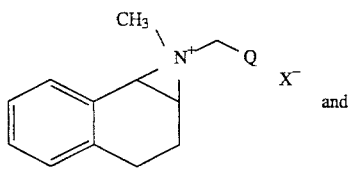
and

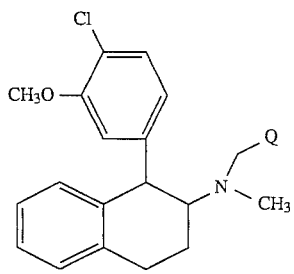

wherein $X^-$ is halide, $BF_4^-$, $R^3SO_3^-$, wherein $R^3$ is $C_1$–$C_6$ alkyl, $CF_3$, $C_1$–$C_6$ alkylphenyl or phenyl, and Q is a group of the formula

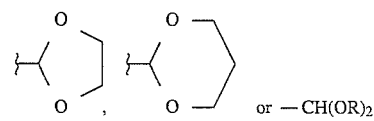 or $-CH(OR)_2$ wherein R is $C_1$–$C_6$ alkyl;
useful for preparing benzazepine intermediates of the formula

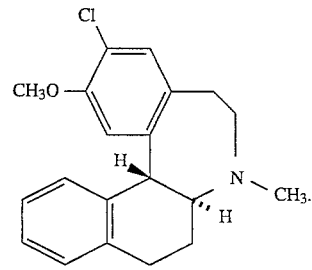

These benzazepine intermediates are useful for preparing benzazepines having activity as selective D1 receptor antagonists.

13 Claims, No Drawings

PROCESS FOR PREPARING BENZAZEPINE INTERMEDIATES FOR THE SYNTHESIS OF D1 ANTAGONISTS

BACKGROUND OF THE INVENTION

The present invention relates to a process for preparing intermediates useful in the preparation of benzazepines having activity as selective D1 receptor antagonists.

U.S. Pat. No. 4,973,586 discloses fused benzazepines, and in particular the compound known as SCH 39166, having the structure

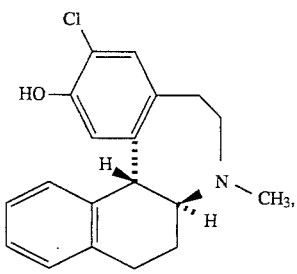

as selective D1 antagonists useful in the treatment of psychoses, depression, pain and D1 dependent neurological disorders. Methods for preparing such compounds are also described therein.

Berger, et al, *J. Med. Chem.*, 2, 1913–1921 (1989), discloses a process for preparing SCH 39166 comprising acid promoted cyclization of a compound of the formula (1) to give a 1:1 mixture of cis and trans benzazepines (cis-2 and trans-2, respectively). Compound trans-2 is then converted to racemic compound I via a multi-step procedure. Compound I is resolved via its di-O,O'-p-tolyltartrate salt and hydrolyzed with HBr and HOAc to give SCH 39166.

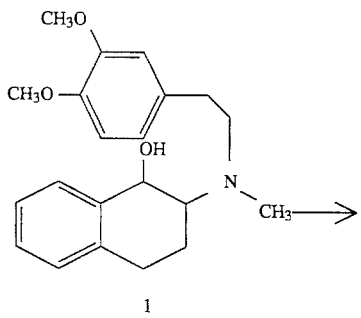

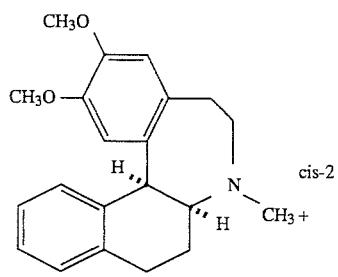

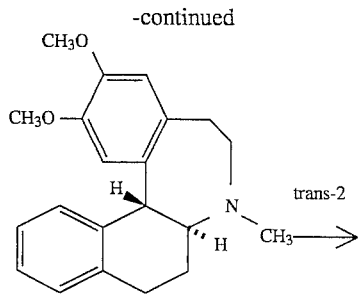

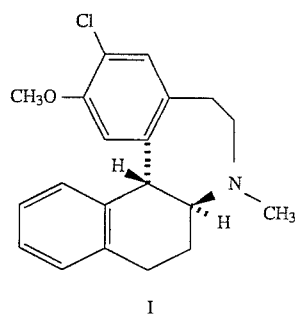

The prior art process suffers from several shortcomings. It is inefficient, producing a 1:1 mixture of cis and trans benzazepines in the cyclization step. In addition, conducting the resolution step at a late stage of the synthesis is very costly and adds further inefficiency. Therefore, it was desirable to develop a chemically efficient and cost effective process for preparing SCH 39166 of high optical purity. It was also desired that the resolution be performed at an early stage of the process or that the chiral centers be introduced using inexpensive chiral starting materials, thereby avoiding the need for resolution.

SUMMARY OF THE INVENTION

The present invention comprises a process for preparing a compound of the formula I

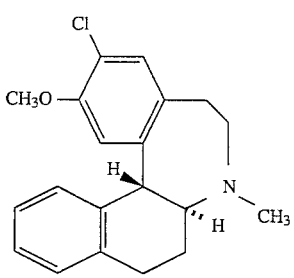

comprising the steps:
(a) Reacting an aziridinium salt of the formula

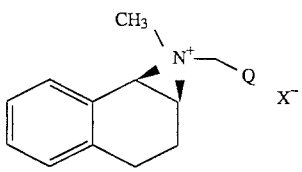

wherein Q is a group of the formula

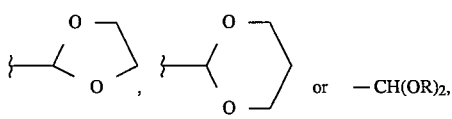

wherein R is $C_1$–$C_6$ alkyl, and $X^-$ is a counterion, with a reagent of the formula

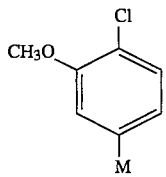

wherein M is selected from MgL, ZnL, TiL$_3$, CeL$_2$, MnL or CuL, and L is a halide selected from Br, Cl or I; to form a compound of the formula

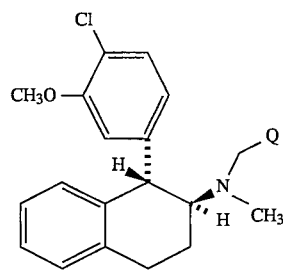

wherein Q is as defined above; and (b) cyclizing the product of step (a).

The present invention further comprises a process, designated Process A, wherein the aziridinium salt of step (a) is prepared, as a racemate or a single enantiomer, by a process comprising the steps:

(A1) epoxidizing 1,2-dihydronaphthalene to form an epoxide of the formula

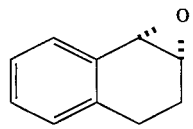

as a racemate by reacting with:
(i) $H_2O_2$ in the presence of a base; or as a single enantiomer by reacting with:
(ii) NaOCl in the presence of Mn(III) salen catalyst; or
(iii) $O_sO_4$ in the presence of NMMO and dihydroquinine 4-chlorobenzoate, followed by treating the resulting cis diol with $(C_6H_5)_3PBr_2$ in the presence of a tertiary amine base;

(A2) regioselectively reacting the epoxide of step (A1) with $CH_3NH_2$ to form an aminoalcohol of the formula

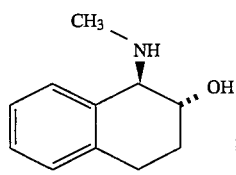

(A3) N-alkylating the aminoalcohol of step (A2) with a compound of the formula J—CH$_2$—Q, wherein J is a leaving group, and Q is as defined above; and (A4) cyclizing the product of step (A3) by treating with an alkyllithium reagent and a sulfonyl chloride.

In an alternative embodiment, the present invention further comprises a process, designated Process B, wherein the aziridinium salt of step (a) is prepared in optically active form by a process comprising the steps:

(B1) Reacting S-(+)-2-amino-4-phenylbutanoic acid with ClCO$_2$R$^2$ to form a carbamate of the formula

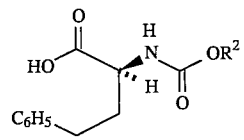

wherein R$^2$ is benzyl or $C_1$–$C_6$ alkyl;

(B2) reacting the carbamate of step (B1) with a chlorinating agent, then cyclizing the resulting acid chloride by treating with a Lewis acid to form a ketone of the formula

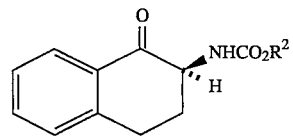

wherein R$^2$ is as defined above;

(B3) reducing the ketone of step (B2) by reacting with a hydride reducing agent to form a compound of the formula

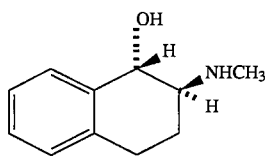

(B4) reacting the product of step (B3) with a compound of the formula J—CH$_2$—Q, wherein J and Q are as defined above; and (B5) cyclizing the product of step (B4) by treating with an alkyllithium reagent and a sulfonyl chloride.

In a second alternative embodiment, the present invention further comprises a process, designated Process C, wherein the aziridinium salt of step (a) is prepared by a process comprising the steps:

(C1) converting 1,2-dihydronaphthalene to an epoxide of the formula

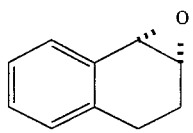

by the process of step (A1);

(C2) reacting the epoxide of step (C1) with an amine of the formula HN(R$^1$)—CH$_2$—Q, wherein R$^1$ is H or CH$_3$, and Q is as defined above, to form an amino alcohol of the formula

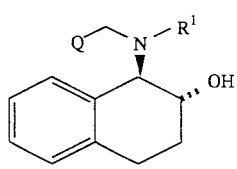

(C3)

(I) where R$^1$ is H, cyclizing the product of step (C2) to form an aziridine of the formula

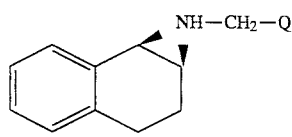

by reacting with:
(i) (C$_6$H$_5$)$_3$PBr$_2$; or
(ii) mesyl chloride or tosyl chloride in the presence of a tertiary amine base;

followed by N-methylating the resulting aziridine by treating with:
(iii) CF$_3$SO$_3$CH$_3$; or
(iv) (CH$_3$)$_3$OBF$_4$; or (II) where R$^1$ is CH$_3$, cyclizing the product of step (C2) by treating with an alkyllithium reagent and a sulfonyl chloride.

In a third alternative embodiment, the present invention further comprises a process, designated Process D, wherein the aziridinium salt of step (a) is prepared in optically active form by a process comprising the steps:

(D1) resolving a trans-amine of the formula

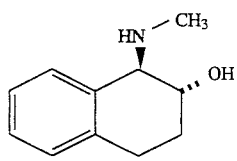

by treating with L-(+)-tartaric acid in an alcohol solvent to form the tartrate salt, recrystallizing the tartrate salt from an alcohol solvent, then treating the tartrate salt with base to form a chiral amine of the formula

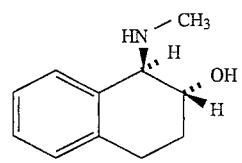

(D2) reacting the chiral amine of step (D1) with a compound of the formula J—CH$_2$—Q, wherein J and Q are as defined above, in the presence of a base to form a compound of the formula

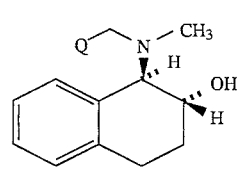

(D3) cyclizing the product of step (D2) by treating with an alkyllithium reagent and a sulfonyl chloride.

Preferred is a process wherein: Q is—CH(OCH$_3$)$_2$; the counterion X$^-$ is Cl$^-$, BF$_4^-$, CH$_3$C$_6$H$_4$SO$_3^-$, C$_6$H$_5$SO$_3^-$, CH$_3$SO$_3^-$ or CF$_3$SO$_3^-$; M is MgBr; and the cyclization of step (b) is carried out by treating with a strong acid, followed by treatment with a hydride reducing agent, preferably BH$_3$.tBuNH$_2$ or NaBH$_4$.

Also preferred is a process according to Process A wherein: the base of step (A 1 )(i) is NaHCO$_3$ or KHCO$_3$; the tertiary amine base of Step (A1)(iii) is Et$_3$N; in Step (A3) J is Br; the alkyllithium reagent of Step (A4) is n-butyllithium; and the sulfonyl chloride of Step (A4) is tosyl chloride, nosyl chloride, brosyl chloride, benzene sulfonyl chloride or mesyl chloride.

Another preferred process is a process according to Process B wherein: the chlorinating agent of step (B2) is oxalyl chloride or SOCl$_2$; the Lewis acid of step (B2) is AlCl$_3$; the hydride reducing agent of step (B3) is LiAlH4; in Step (B4) J is Br; the alkyllithium reagent of Step (B5) is n-butyllithium; and the sulfonyl chloride of Step (B5) is tosyl chloride, nosyl chloride, brosyl chloride, benzene sulfonyl chloride or mesyl chloride.

Yet another preferred process is a process according to Process C wherein: the tertiary amine base of step (C3)(ii) is Et$_3$N; the alkyllithium reagent of Step (C3)(II) is n-butyllithium; and the sulfonyl chloride of Step (C3)(II) is tosyl chloride, nosyl chloride, brosyl chloride, benzene sulfonyl chloride or mesyl chloride.

Still another preferred process is a process according to Process D wherein the alcohol solvent of step (D1) is methanol; the base of step (D2) is NH$_4$OH, Na$_2$CO$_3$ or K$_2$CO$_3$; J is Br; the alkyllithium of step (D3) is n-butyllithium; and the sulfonyl chloride of Step (D3) is tosyl chloride, nosyl chloride, brosyl chloride, benzene sulfonyl chloride or mesyl chloride.

The process of the present invention does not suffer the shortcomings of the prior art processes. It is chemically efficient and, by utilizing inexpensive chiral starting materials, or by utilizing enantioselective transformations on prochiral compounds, or alternatively by performing a resolution step at an early stage of the synthesis, produces a chiral product (compound I) which is readily converted to SCH 39166 by known methods.

The present invention further comprises compounds of the formula

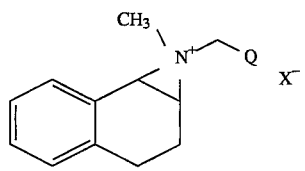

wherein: X⁻ is halide, $BF_4^-$ or $R^3SO_3^-$, wherein $R^3$ is $C_1$–$C_6$ alkyl, $CF_3$, benzyl, phenyl or Z-substituted phenyl, wherein Z is $C_1$–$C_6$ alkyl, nitro or bromo; and Q is a group of the formula

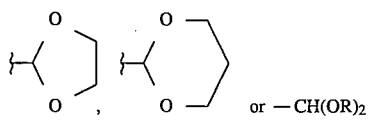

wherein R is $C_1$–$C_6$ alkyl, useful as intermediates in the preparation of benzazepines having activity as selective D1 receptor antagonists. Preferably such compounds have the absolute stereochemistry shown in the formula

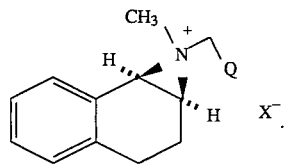

The present invention also comprises compounds of the formula

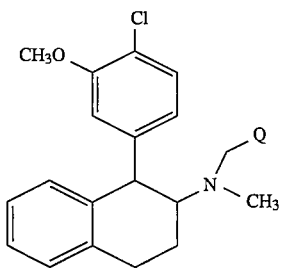

wherein Q is a group of the formula

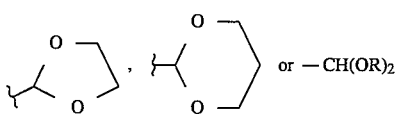

wherein R is $C_1$–$C_6$ alkyl, useful as intermediates in the preparation of benzazepines having activity as selective D1 receptor antagonists. Preferably such intermediates have the absolute stereochemistry shown in the formula

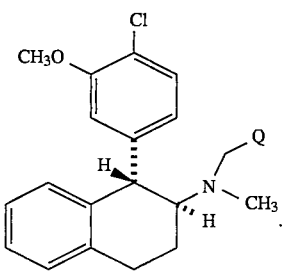

In another embodiment, the present invention comprises chiral compounds of the formula

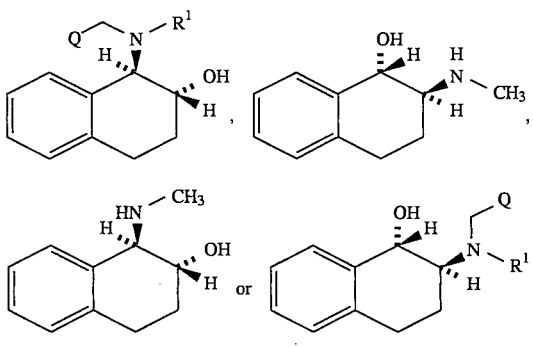

wherein $R^1$ is H or $CH_3$; and Q is a group of the formula

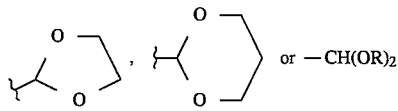

wherein R is $C_1$–$C_6$ alkyl, useful as intermediates in the preparation of benzazepines having activity as selective D1 receptor antagonists.

DETAILED DESCRIPTION

In general, stereochemical representations are meant to denote relative stereochemistry. However, where optically active starting materials are employed, such as in the embodiment denoted as process B, the stereochemical representations denote absolute as well as relative stereochemistry. Therefore, by using such optically active starting materials, compounds of the formula I can be prepared as a single enantiomer. Similarly, by utilizing stereoselective transformations on prochiral compounds to generate chiral compounds, or by performing a resolution step (such as in Process D), a single enantiomer of compounds of the formula I is produced.

In those embodiments where the present invention relates to chiral compounds, the stereochemical purity of such compounds is generally given in terms of the enantiomeric excess (e.e.).

As used herein the term "alkyl" means a straight or branched alkyl chains of 1 to 6 carbon atoms;

"tertiary amine base" means a tertiary amine selected from pyridine, di-isopropylethylamine or a tri-($C_1$–$C_6$ alkyl)amine, such as triethylamine;

"base" means a water soluble base, such as NH$_4$OH, KHCO$_3$, K$_2$CO$_3$, NaHCO$_3$ or Na$_2$CO$_3$;

"strong base" means an alkali metal hydroxide, such as NaOH, KOH or LiOH, or an alkaline earth metal hydroxide such as Ca(OH)$_2$;

"leaving group" means a group which can be readily displaced by a nucleophile, preferably —Cl, —Br, —I, —OSO$_2$CH$_3$, —OSO$_2$CF$_3$ or —OSO$_2$C$_6$H$_4$CH$_3$;

"sulfonyl chloride" means a compound of the formula R$^3$SO$_2$Cl, wherein R$^3$ is C$_1$–C$_6$ alkyl, CF$_3$, benzyl, phenyl or Z-substituted phenyl, and Z is C$_1$–C$_6$ alkyl, nitro or bromo, with preferred sulfonyl chlorides including tosyl chloride, nosyl chloride, mesyl chloride, brosyl chloride and benzene sulfonyl chloride;

"alkyllithium" means an alkyllithium reagent, such as n-butyllithium, methyllithium, sec-butyllithium or tert-butyllithium;

"strong acid" means a protic acid having a pKa<2, such as H$_2$SO$_4$ or CH$_3$SO$_3$H;

"Lewis acid" means a Lewis acid capable of catalyzing a Friedel-Crafts type reaction, such as AlCl$_3$;

"hydride reducing agent" means a metal hydride reducing agent, such as NaBH$_4$, NaBH$_3$CN, LiBH$_4$ or LiAlH$_4$, or a borane amine complex, such as borane-methylamine, borane-tert-butylamine, borane-piperidine, borane-triethylamine, borane-N,N-diisopropylethylamine, borane-N,N-diethylaniline, borane-morpholine, borane-4-ethylmorpholine or borane-4-phenylmorpholine complex;

"counterion" means an anion selected from a halide, BF$_4^-$, and R$^3$SO$_3^-$, wherein R$^3$ is C$_1$–C$_6$ alkyl, CF$_3$, C$_1$–C$_6$ alkylphenyl, benzyl, nitrophenyl, bromophenyl or phenyl; and "halide" means a chloride, bromide, fluoride or iodide anion.

As used herein the following reagents and solvents are identified by the abbreviations indicated: para-toluenesulfonyl chloride (tosyl chloride, TsCl); para-bromobenzenesulfonyl chloride (brosyl chloride); para-nitrobenzenesulfonyl chloride (nosyl chloride); N-methylmorpholine-N-oxide (NMMO); methanesulfonyl chloride (mesyl chloride, MsCl); tetrahydrofuran (THF); iso-propanol (i-PrOH); methanol (MeOH); ethyl acetate (EtOAc); tert-butyl methyl ether (TBME); borane-tert-butylamine complex (BH$_3$.tBuNH$_2$); triethylamine (Et$_3$N); chloro[[2,2'-[1,2-cyclohexane-diylbis(nitrilomethylidyne)]bis[4,6-bis(1,1 -dimethyl-ethyl)phenolato]](2-)-N, N', O,O'-manganese (Mn(III) salen catalyst); trifluoroacetic acid (TFA).

The aziridinium salts of step(a) of the process of the present invention exist in conjunction with a counterion identified as X$^-$. The counterion is a suitable anion such as halide, BF$_4^-$ or R$^3$SO$_3^-$, wherein R$^3$ is C$_1$–C$_6$ alkyl, CF$_3$, C$_1$–C$_6$ alkylphenyl, benzyl, nitrophenyl, bromophenyl or phenyl.

The present invention comprises a process for preparing a compound of the formula I as shown in Reaction Scheme 1. The stereochemical representations depict the preferred stereoisomers. The process can be carried out using a racemic aziridinium salt, in which case the stereochemical representations designate the preferred isomers having the relative stereochemistry shown. Alternatively, the process can utilize a single enantiomeric aziridinium salt to produce a single enantiomer of compound I, wherein the stereochemical representations further designate absolute stereochemistry.

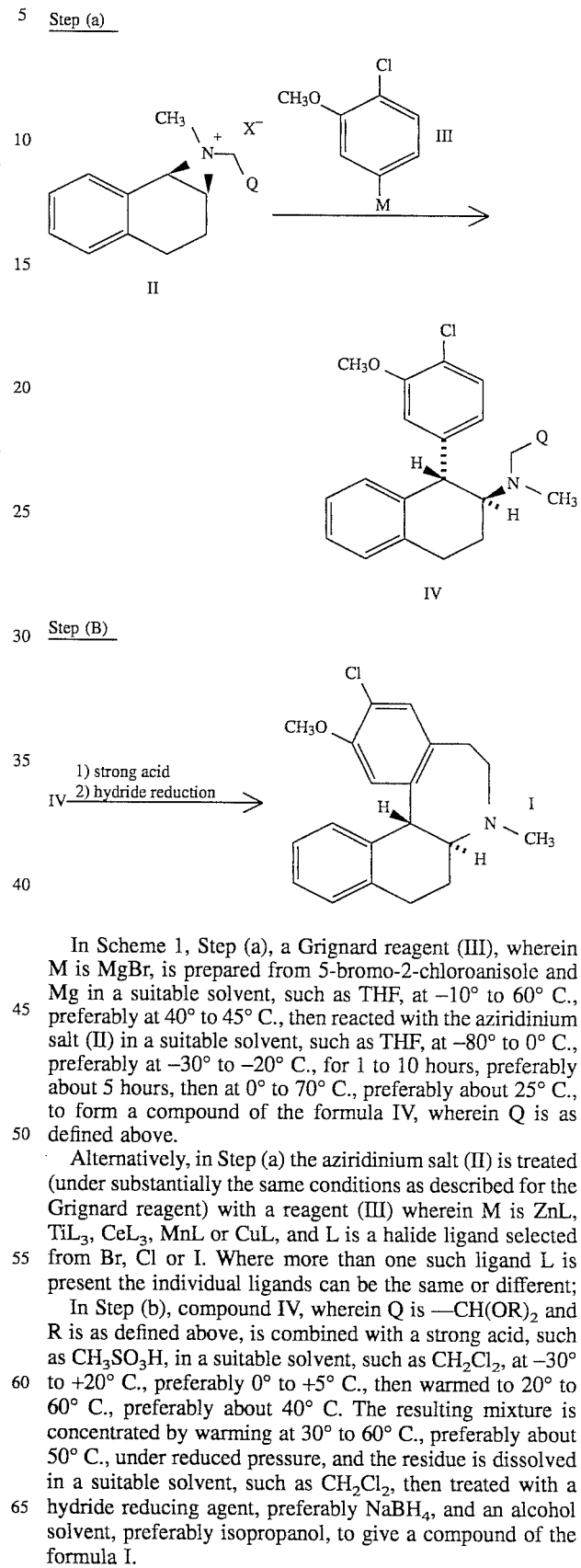

In Scheme 1, Step (a), a Grignard reagent (III), wherein M is MgBr, is prepared from 5-bromo-2-chloroanisole and Mg in a suitable solvent, such as THF, at −10° to 60° C., preferably at 40° to 45° C., then reacted with the aziridinium salt (II) in a suitable solvent, such as THF, at −80° to 0° C., preferably at −30° to −20° C., for 1 to 10 hours, preferably about 5 hours, then at 0° to 70° C., preferably about 25° C., to form a compound of the formula IV, wherein Q is as defined above.

Alternatively, in Step (a) the aziridinium salt (II) is treated (under substantially the same conditions as described for the Grignard reagent) with a reagent (III) wherein M is ZnL, TiL$_3$, CeL$_3$, MnL or CuL, and L is a halide ligand selected from Br, Cl or I. Where more than one such ligand L is present the individual ligands can be the same or different;

In Step (b), compound IV, wherein Q is —CH(OR)$_2$ and R is as defined above, is combined with a strong acid, such as CH$_3$SO$_3$H, in a suitable solvent, such as CH$_2$Cl$_2$, at −30° to +20° C., preferably 0° to +5° C., then warmed to 20° to 60° C., preferably about 40° C. The resulting mixture is concentrated by warming at 30° to 60° C., preferably about 50° C., under reduced pressure, and the residue is dissolved in a suitable solvent, such as CH$_2$Cl$_2$, then treated with a hydride reducing agent, preferably NaBH$_4$, and an alcohol solvent, preferably isopropanol, to give a compound of the formula I.

Alternatively, in Step (b), compound IV, wherein Q is —CH(OR)$_2$ and R is as defined above, is combined with a strong acid, such as H$_2$SO$_4$, in a suitable solvent, such as CH$_2$Cl$_2$, at −20° to +20° C., preferably 0° to +5° C., then warmed to 10° to 60° C., preferably about 25° C. The mixture is cooled to −20° to +20° C., preferably about 0° C., then treated with a hydride reducing agent, preferably BH$_3$.tBuNH$_2$, and warmed to 10° to 60° C., preferably about 25° C., to give a compound of the formula I.

The present invention further comprises a process as described above wherein the aziridinium salt of Step (a) is prepared according to Process A, as shown in Reaction Scheme A.

Reaction Scheme A

Step A1

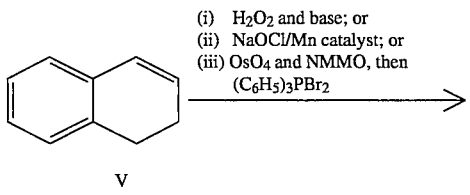

V (i) H$_2$O$_2$ and base; or
(ii) NaOCl/Mn catalyst; or
(iii) OsO$_4$ and NMMO, then (C$_6$H$_5$)$_3$PBr$_2$

VI

Step A2

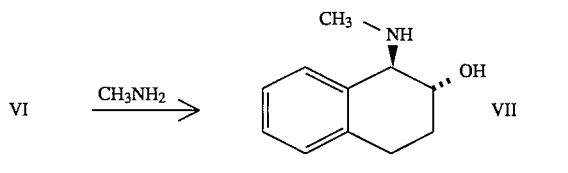

VI  $\xrightarrow{\text{CH}_3\text{NH}_2}$  VII

Step A3

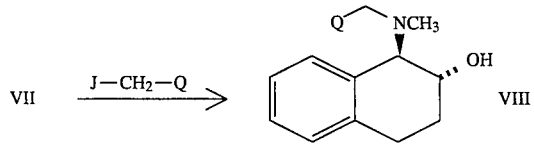

VII  $\xrightarrow{\text{J—CH}_2\text{—Q}}$  VIII

Step A4

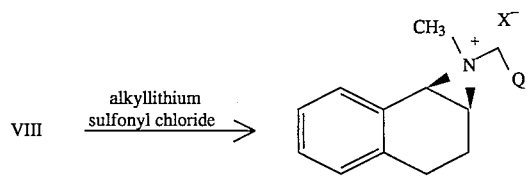

VIII  $\xrightarrow[\text{sulfonyl chloride}]{\text{alkyllithium}}$  II

In Reaction Scheme A, Step A1, 1,2-dihydronaphthalene (V) is treated with H$_2$O$_2$, preferably 30% H$_2$O$_2$ (aqueous), and a base, preferably KHCO$_3$ or NaHCO$_3$, in a suitable solvent, such as a mixture of CH$_3$CN and an alcohol solvent, preferably CH$_3$CN and MeOH, at 0° to 50° C., preferably at 25° to 30° C., for 2 to 24 hours, preferably about 17 hours, to form the racemic epoxide VI.

Alternatively, 1,2-dihydro-naphthalene (V) is converted to a single enantiomer of the epoxide VI as described in Step C1 of Method C.

In Step A2, the epoxide VI is reacted with CH$_3$NH$_2$ in a suitable sealed container, preferably a teflon® lined bomb, at 50° to 130° C., preferably at 80° to 110° C., and most preferably about 100° C., for 12 to 36 hours, preferably about 22 hours, to form the aminoalcohol VII.

Alternatively, in Step A2, the epoxide VI is reacted with an excess of 40% CH$_3$NH$_2$ (aqueous) at 0° to 50° C., preferably about 25° C., for 12 to 36 h, preferably about 24 h, to form the aminoalcohol VII. The reaction is carried out via substantially the same procedure as described in Crabb, et al., Mag. Res. in Chem., 24, 798 (1986) and Lukes, et al., Coil. Czech. Chem. Comm., 25, 492 (1960).

In Step A3, compound VII is combined with a compound of the formula J—CH$_2$—Q, wherein J and Q are as defined above, in a suitable solvent, such as CH$_3$CN or DMF, in the presence of a base, preferably Na$_2$CO$_3$ or K$_2$CO$_3$, and the resulting mixture heated at 30° to 100° C., preferably at reflux, for 1 to 8 days, preferably about 6 days, to form compound VIII.

In Step A4, compound VIII is treated with an alkyllithium, preferably n-butyllithium, in a suitable solvent, such as anhydrous THF, at −60° to +20° C., preferably about 0° C., for about 10 minutes. The resulting mixture is then treated with a sulfonyl chloride, preferably tosyl chloride, at −20° to +20° C., preferably about 0° C., for about 15 minutes to form the aziridinium salt II, wherein Q is as defined above, and X$^-$ is R$^3$SO$_3^-$, wherein R$^3$ is as defined above, which is used directly in Step (a) above.

In an alternative embodiment, the present invention further comprises a process as described in Reaction Scheme 1 wherein a single enantiomer of the aziridinium salt of Step (a) is prepared according to Process B as shown in Reaction Scheme B.

Reaction Scheme B

Step B1

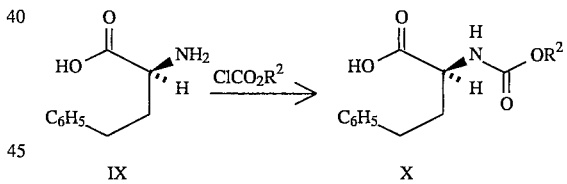

IX  $\xrightarrow{\text{ClCO}_2\text{R}^2}$  X

Step B2

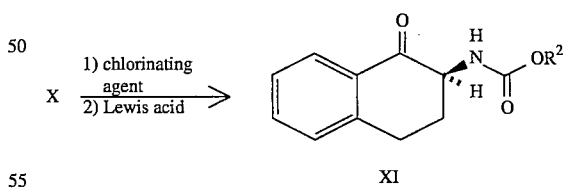

X  $\xrightarrow[\text{2) Lewis acid}]{\text{1) chlorinating agent}}$  XI

Step B3

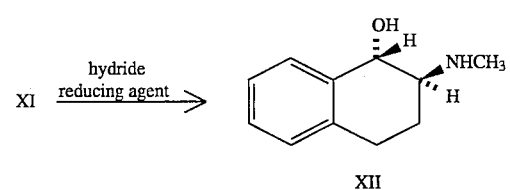

XI  $\xrightarrow{\text{hydride reducing agent}}$  XII

Step B4

-continued
Reaction Scheme B

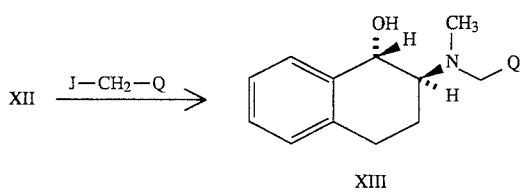

XIII

Step B5

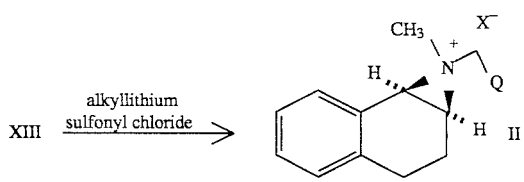

Reaction Scheme C

Step C1

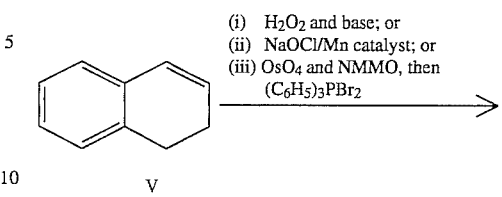

Step C2

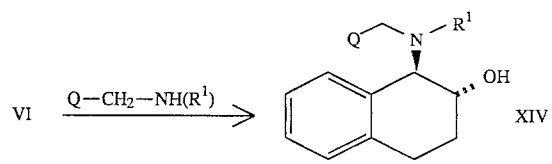

Step C3 (I)

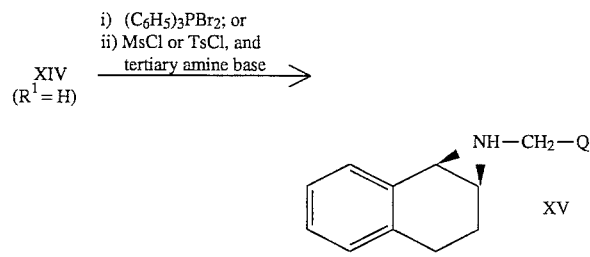

Step C3 (II)

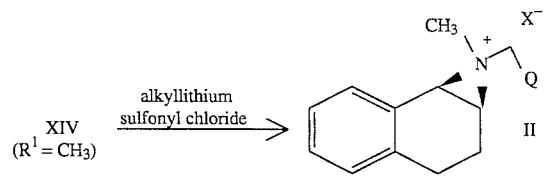

In Reaction Scheme B, Step B1, a combination of the chiral amino acid IX, a strong base, preferably NaOH, most preferably 1N aqueous NaOH, and a base, preferably $Na_2CO_3$, at $-20°$ to $+20°$ C., preferably about $0°$ C., is treated with $ClCO_2R^2$, wherein $R^2$ is as defined above, preferably $CH_3$, then warmed to $0°$ to $40°$ C., preferably about $25°$ C., for 1 to 5 hours, preferably about 3 hours, then treated with HCl to form the carbamate X.

In step B2, the carbamate X is combined with a chlorinating agent, such as $SOCl_2$ or oxalyl chloride, preferably $SOCl_2$, in a suitable solvent, such as $CH_2Cl_2$, and heated at $30°$ to $70°$ C., preferably at reflux, for 1 to 10 hours, preferably about 3 hours, then cooled to about $25°$ C. The resulting mixture is treated with a Lewis acid, preferably $AlCl_3$, in a suitable solvent, such as $CH_2Cl_2$, for 1 to 10 hours, preferably about 3 hours, to give the ketone of the formula XI.

In Step B3, the ketone XII is treated with a hydride reducing agent, preferably $LiAlH_4$, in a suitable solvent, such as THF, at $-60°$ to $20°$ C., preferably about $0°$ C., for about 1 hour, then heated at $30°$ to $80°$, preferably at reflux, for 1 to 10 hours, preferably about 2 hours, to form a compound of the formula XII.

In Step B4, compound XII is treated with a compound of the formula J—$CH_2$—Q, wherein J and Q are as defined above, in a suitable solvent, such as $CH_3CN$, in the presence of $K_2CO_3$, $Na_2CO_3$ or KF and alumina, and the resulting mixture heated at $40°$ to $120°$ C., preferably at reflux, for 1 to 4 days, preferably about 2 days, to form compound XIII.

In Step B5, compound XIII is treated with an alkyllithium, preferably n-butyllithium, in a suitable solvent, such as THF, at $-60°$ to $+20°$ C., preferably about $0°$ C., for about 10 minutes. The resulting mixture is then treated with a sulfonyl chloride, preferably tosyl chloride, at $-20°$ to $+20°$ C., preferably about $0°$ C., for about 15 minutes to form a single enantiomer of the aziridinium salt II, wherein Q is as defined above, $X^{31}$ is $R^3SO_3^-$, wherein $R^3$ is as defined above, and wherein the absolute stereochemistry is as shown in Reaction Scheme B, which is used directly in Step (a) of Reaction Scheme 1 above.

In a second alternative embodiment, the present invention further comprises a process as described in Reaction Scheme 1 wherein the aziridinium salt of Step (a) is prepared according to Process C as shown in Reaction Scheme C.

In Reaction Scheme C, Step C1: 1,2-dihydronaphthalene (V) is converted to the racemic epoxide VI as described above for Step A1 of Method A.

Alternatively, 1,2-dihydronaphthalene (V) is treated with $OsO_4$ and NMMO in a suitable solvent, such as a mixture of acetone and water, at $-60°$ to $+20°$ C., preferably at about $0°$ C., for 10 to 48 hours, preferably about 26 hours, to give cis-1,2,3,4-tetrahydro-1,2-napthalenediol. The treatment with OsO4 and NMMO can optionally be carried out in the presence of hydroquinine 4-chlorobenzoate, as described in Sharpless, et al, *J. Org. Chem.*, 57, 2768–2771 (1992), in which case predominantly one enantiomer of the cis-diol is produced. The diol is treated with $(C_6H_5)_3PBr_2$ in the presence of a tertiary amine base, preferably triethylamine, in a suitable solvent, such as CH₃CN, at 0° to 50° C., preferably at about 25° C., for 10 to 30 hours, preferably about 20 hours, to form predominantly one enantiomer of the epoxide VI, having the absolute stereochemistry indicated in Reaction Scheme C.

In another alternative, 1,2-dihydronaphthalene (V) is treated with NaOCl, preferably an aqueous solution of NaOCl, and a suitable manganese catalyst, preferably chloro[[2,2'-[1,2-cyclohexanediylbis(nitrilomethylidene)]bis[4,6-bis(1,1-dimethylethyl)phenolato]] (2-)-N,N',O,O'-manganese, as described in Zhang, et al, *J. Org. Chem.*, 56 2296–2298 (1991). The reaction is carried out in a suitable solvent, such as CH₂Cl₂, in the presence of 4-phenylpyridine N-oxide, at –60° to +20° C., preferably at about 0° C., for 30 to 90 minutes, preferably about 45 minutes, to form the chiral epoxide VI, 90% e.e., having the absolute stereochemistry indicated in Reaction Scheme C.

The epoxide VI can also be obtained as a single stereoisomer from commercial sources for use in Step C2.

In Step C2, the epoxide VI is treated with an amine of the formula Q—CH₂—NH(R¹), wherein Q and R¹ are as defined above, in a sealed container, preferably in a Teflon® lined bomb, at 60° to 120° C., preferably at about 95° C., for 10 to 48 hours, preferably for 20 to 24 hours, to form compound XIV.

In Step C3 (I), compound XIV, wherein R¹ is H, is reacted with (C₆H₅)₃PBr₂ and a tertiary amine base, preferably triethylamine, in a suitable solvent, such as CH₃CN, at –40° to +20° C., preferably at about 0° C., for 1 to 2 hours, preferably about 90 minutes to form the aziridine XV. Alternatively, compound XIV is converted to the aziridine XV by treating with MsCl or TsCl and a tertiary amine base, preferably triethylamine, in a suitable solvent. Aziridine XV is reacted with (CH₃)₃OBF₄ in a suitable solvent, such as CH₂Cl₂, at –60° to 0° C., preferably at about –20° C., for 10 to 30 hours, preferably about 20 hours, to form the aziridinium salt II, wherein X⁻ is BF₄⁻. Alternatively, the aziridine XV is treated with CF₃SO₃CH₃ in a suitable solvent, such as THF, at 0° to 50° C., preferably at about 25° C., for 10 to 60 minutes, preferably about 20 minutes, to form the aziridinium salt II, wherein X⁻ is CF₃SO₃⁻.

In Step C3 (II), compound XIV is converted to the aziridinium salt II as described for Step A4 of Method A.

In a third alternative embodiment, the present invention further comprises a process as described in Reaction Scheme 1 wherein a single enantiomer of the aziridinium salt of Step (a) is prepared according to Process D as shown in Reaction Scheme D.

Reaction Scheme D

Step D1

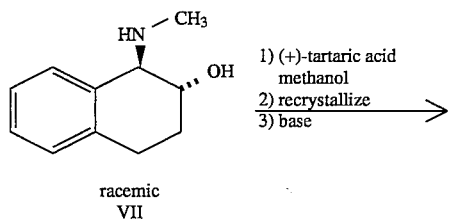

1) (+)-tartaric acid methanol
2) recrystallize
3) base racemic
VII

-continued
Reaction Scheme D

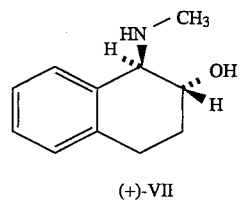

(+)-VII

Step D2

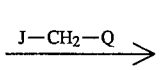

(+)-VII  J—CH₂—Q →

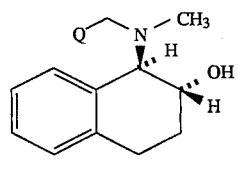

VIII

Step D3

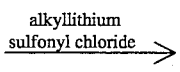

VIII  alkyllithium sulfonyl chloride →

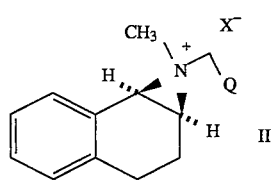

II

In Reaction Scheme D, In Step D1, the racemic transamine VII is treated with L-(+)-tartaric acid in a alcohol solvent, preferably methanol, at 0° to 50° C., preferably about 20° C., to form a solution of the tartrate salt. The tartrate salt solution is cooled to –20° to +20° C., preferably about –5° C., to give the crystalline tartrate salt. The tartrate salt is dissolved in an alcohol solvent, preferably methanol, at 30° to 100° C., preferably at reflux temperature, then cooled to –20° to +20° C., preferably about –5° C., to give the recrystallized tartrate salt. The recrystallized tartrate salt is treated with a base, preferably 10% NH₄OH (aqueous) to give the amine (+)–VII as a single enantiomer.

In Step D2, the amine (+)–VII is converted to a single enantiomer of compound VIII via the process described for Step A3 of Reaction Scheme A.

In Step D3, compound VIII is converted to the aziridinium salt II as described for Step A4 of Reaction Scheme A.

Starting compounds of the formula V, IX and XVIII are commercially available. Compounds of the formula J—CH₂—Q are commercially available or can be prepared via known methods, such as the methods described by Gribble, et al, in *J. Org. Chem.*, 46, 2433–2434 (1981). Compounds of the formula VII can be prepared as described above or by Process E as shown in Reaction Scheme E.

Reaction Scheme E

Step E1

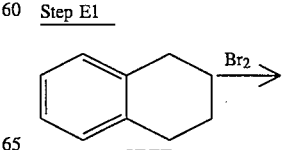  Br₂ →

XVIII

-continued
Reaction Scheme E

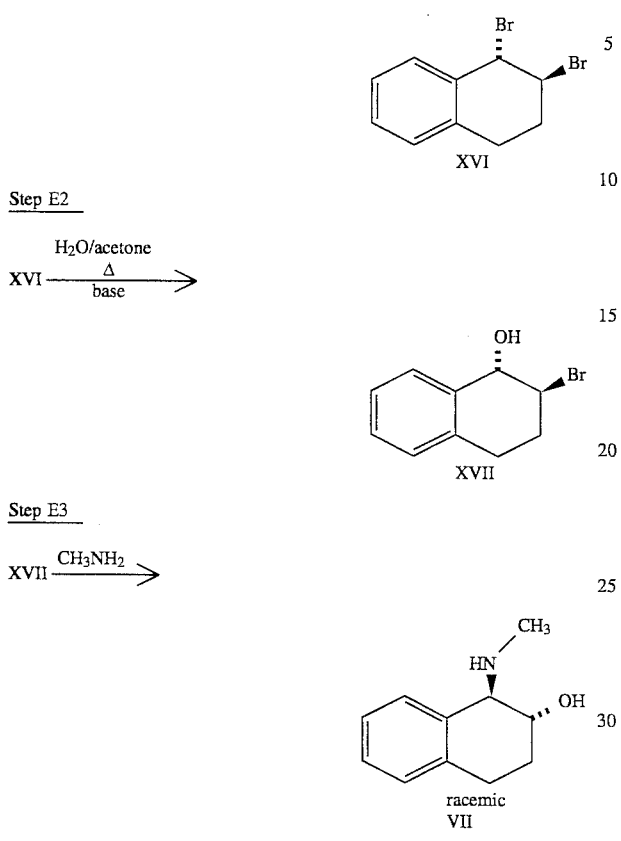

The conversion of XVIII to VII is carried out via substantially the same procedures as described by: Braun, et al., *Chem Berichte*, 54, 597 (1921); Braun, et al., *Chem Berichte*, 55, 3648 (1922); and Lukes, et al., Coil. Czech. Chem. Comm., 492 (1960).

In Step E1, 1,2,3,4-tetra-hydronaphthalene XVIII is treated with $Br_2$ at 60° to 110° C., preferably about 90° C., to form the racemic trans-dibromide XVI.

Alternatively, in Step E 1, a solution of compound XVIII in hexane is treated with $Br_2$ at 40° C. to 100° C., preferably at reflux temperature, to form the racemic trans-dibromide XVI.

In Step E2, the dibromide XVI is combined with a mixture of acetone, water and a base, preferably $NaHCO_3$, and heated at 40° to 100° C., preferably at reflux temperature, for 1 to 6 h, preferably about 3 h, to form the racemic trans-alcohol XVII.

In Step E3, the alcohol XVII is reacted with a 40% solution of $CH_3NH_2$ in water at 0° to 50° C., preferably about 20° C., for 10 to 30 h, preferably about 16 h, to form the racemic trans-amine VII.

The following examples illustrate the process of this invention:

PREPARATION 1

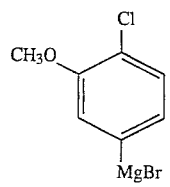

Combine Mg turnings (1.30 g, 54.00 mmol) and 35 mL dry THF. Add a solution of 5-bromo-2-chloroanisole (11.78 g, 53.20 mmol) dissolved in 300 mL dry THF over a 10 min. period, maintaining the reaction temperature at 40°–45° C., and stir for 90 min. The resulting solution of Grignard reagent is used as is.

PREPARATION 2

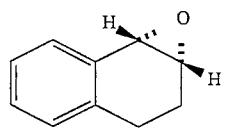

Step (a):

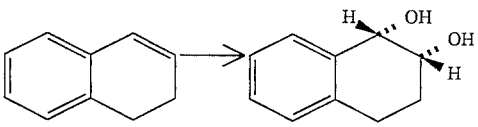

Combine hydroquinine 4-chlorobenzoate (5.00 g, 10.753 mmol), NMMO (7.57 g, 64.636 mmol) and 44 mL of a 10:1 acetone/water solution, stir vigorously and add $OsO_4$ (0.35 mL, 0.175 mmol, 0.5M in toluene). Cool to 0° C. and add 1,2-dihydronaphthalene (5.234 g, 40.205 mmol) via a syringe pump over a 10 h period. After 16 h more, add $Na_2S_2O_5$ (13 g), stir for 10 min at room temperature, then add 80 mL of $CH_2Cl_2$ and filter. Wash the solids with 3×50 mL $CH_2Cl_2$, dry the combined filtrates over anhydrous $MgSO_4$ and concentrate in vacuo to a residue. Flash chromatograph the residue (silica gel, 10% to 100% EtOAc/hexanes) and then recrystallize (EtOAc/hexanes) to yield the chiral diol product. $^1H$ NMR ($CDCl_3$) δ7.40 (m, 1H); 7.23 (m, 2H); 7.12 (m, 1H); 4.72 (d, 1H, J=2 Hz); 3.94 (m, 1H); 3.92 (m, 1H); 3.78 (m, 3H); 1.95 (m, 2H). Chiral $^1H$ NMR using a $Eu(hfc)_3$ shift reagent indicated an enantiomeric excess of 24%.

Step (b):

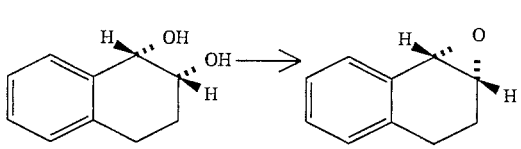

Combine the product of Step (a) (1.678 g, 10.224 mmol) and 50 mL of $CH_3CN$. Add a slurry of $(C_6H_5)_3PBr_2$ (4.371 g, 10.354 mmol) in 10 mL $CH_3CN$ and stir for 30 min. Add a solution of $Et_3N$ (2.335 g, 23.073 mmol) in 10 mL $CH_3CN$ and stir for 20 h. Add the reaction mixture to a mixture of 25 mL saturated NaHCO$_3$, 10 mL H$_2$O and 50 mL TBME. Separate, extract the aqueous layer with 1×25 mL TBME, wash the combined organic layers with 1×25 mL brine, dry over anhydrous MgSO$_4$ and concentrate in vacuo to a residue. Add 75 mL hexanes to the residue, decant from the resulting precipitate, concentrate the hexanes layer and flash chromatograph (silica gel, 5% to 50% EtOAc/hexanes) to afford the title epoxide. $^1$H NMR was identical to the racemic material prepared in Example 2, Step (a).

PREPARATION 3

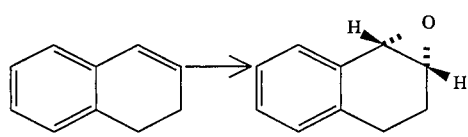

Combine 1,2-dihydronaphthalene (1.000 g, 7.690 mmol), 4-phenylpyridine N-oxide (0.263 g, 1.538 mmol), the (S,S)-isomer of the Mn(III) salen catalyst (0.196 g, 0.310 mmol) and 8 mL of CH$_2$Cl$_2$, and cool to 0° C. Add a cooled solution (0° C.) of NaOCl* (27 mL, 1.105 g, 14.850 mmol, ≈4% NaOCl in water) and stir for 45 min at 0° C. Then extract with 100 mL of hexanes, wash the organic layer with 2×100 mL water and 1×75 mL brine. Extract the combined aqueous washes with 2×30 mL hexanes, and dry the combined organic layers over anhydrous MgSO$_4$. Concentrate in vacuo to a residue, then flash chromatograph (as described in Preparation 2) to afford the chiral epoxide. $^1$H NMR was identical to the racemic material prepared in step C. Chiral HPLC (Daicel OB® column) indicated the product to have an e.e. of 91%.

*Prepare a stock solution of NaOCl by adjusting the pH of 500 mL of NaOCl (Clorox®) to pH 11.3 using 0.05M NaHPO$_4$ and 1M NaOH solutions.

EXAMPLE 1

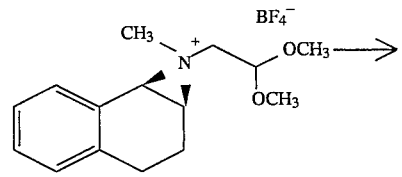

Step (a):

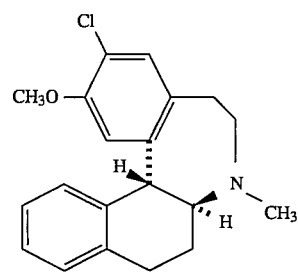

-continued

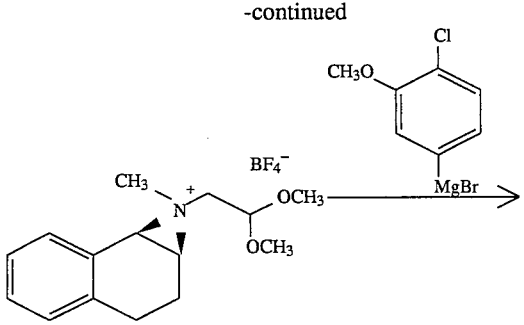

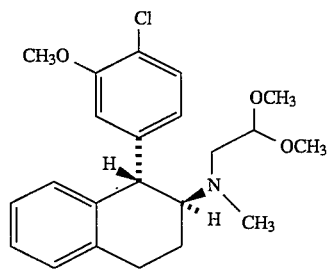

Combine the aziridinium tetrafluoroborate salt of Example 4 (13.70 g, 40.90 mmol) and 70 mL dry THF to form a suspension. Cool to −20° to −30° C. and add the Grignard reagent of Preparation 1 (335 mL, 53.20 mmol, 0.159M in THF) over a 30 min. period. Stir the reaction mixture at −20° C. for 5 h, warm to room temperature, and stir for 15 h more. Cool to 0° to 10° C. and add 8.6% aqueous NaHCO$_3$ to adjust the mixture to pH 11. Extract with 3×100 mL EtOAc, wash the combined organic layers with 1×100 mL water and concentrate to a residue. Purify by flash chromatography (silica gel, 2.5–10% MeO/CH$_2$Cl$_2$) to give the (+)-enantiomer of the title compound. $^1$H NMR (CDCl$_3$) δ: 6.65–7.30 (m, 7H); 4.12 (t, $^1$H, J=5.6 Hz); 4.09 (d, $^1$H, J=11.3 Hz); 3.82 (s, 3H); 3.21 (s, 3H); 3.12 (s, 3H); 2.95 (m, 3H); 2.60 (dd, 2H, J=5.6, 11.3 Hz); 2.31 (s, 3H); 2.08 (m, $^1$H); 1.70–1.80 (m, $^1$H).

Step (b):

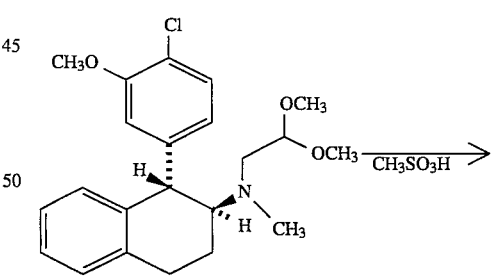

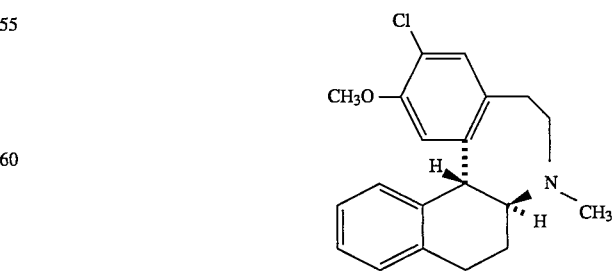

Combine methanesulfonic acid (7.40 g, 77.003 mmol) and 15 mL CH$_2$Cl$_2$ and cool to 0° to 5° C. Dissolve the product of Step (a) (2.34 g, 6.001 mmol) in 15 mL CH$_2$Cl$_2$ and add the resulting solution to the acid solution over a 5 min period. Heat the mixture at 40° C. for 2 h, then concentrate (50° C./20 Torr) to a residue. Dissolve the residue in 10 mL CH$_2$Cl$_2$, cool to 10° to 15° C., and add a solution of NaBH$_4$ (0.280 g, 7.402 mmol) in 15 mL i-PrOH over a 10 min period. Stir for 2 h, then add a solution of Na$_2$CO$_3$ (6.70 g, 63.208 mmol) in 34 mL water to adjust to pH 7. Extract the aqueous layer with 2×10 mL CH$_2$Cl$_2$, wash the combined organic layers with 2×10 mL water, then dry over anhydrous MgSO$_4$ and concentrate in vacuo to yield the (−)-enantiomer of the title compound. Purify by flash chromatography (silica gel, 2.5–10% MeOH/CH$_2$Cl$_2$). $^1$H NMR (CDCl$_3$) δ6.95–7.19 (m, 5H); 5.88 (s, $^1$H); 4.78 (d, $^1$H, J=7.5 Hz); 3.5–3.62 (m, $^1$H); 3.49 (s, 3H); 3.2 (dd, $^1$H, J=3.75, 11.3 Hz); 2.65–2.86 (m, 4H); 2.51 (s, 3H); 2.41 (dd, $^1$H, J=5.6, 11.3 Hz); 1.98–2.18 (m, $^1$H); 1.6–1.8 (dq, $^1$H, J=5.6, 11.3 Hz).

EXAMPLE 1A

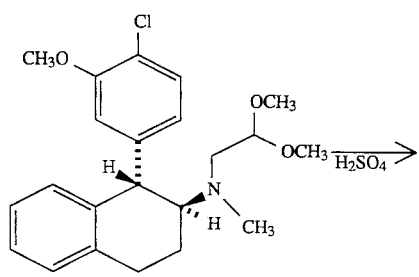

Combine sulfuric acid (11.4 g, 116 mmol) and 200 mL of CH$_2$Cl$_2$ and cool the mixture to 0° C. Dissolve the product of Example 1, Step (a), (9.08 g, 23.3 mmol) in 200 mL of CH$_2$Cl$_2$ and add the resulting solution to the acid mixture. Warm to room temperature, stir for 24 h., then cool to 0° C. and add BH$_3$.tBuNH$_2$ (2.43 g, 27.9 mmol) in portions. Warm to room temperature and stir for 4.5 h, then cool to 0° C. and extract with 150 mL of 1.5M Na$_2$CO$_3$ (aqueous). Wash the organic layer with brine, dry over Na$_2$SO$_4$, then concentrate in vacuo to give the (−)-enantiomer of the title compound. $^1$H NMR matches material prepared in Example 1.

EXAMPLE 2

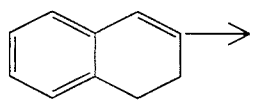

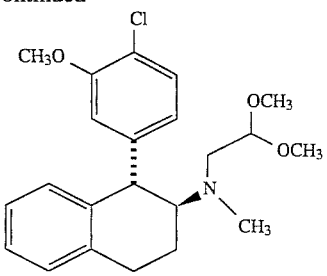

Step (a):

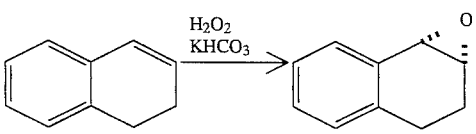

Combine 1,2-dihydronaphthalene (24.20 g, 0.186 mol), 70 mL MeOH and 60 mL CH$_3$CN. Add KHCO$_3$ (2.00 g, 0.020 mol), stir 5 min and then add 30% H$_2$O (45.00 g, 0.400 mol, 30% solution in H$_2$O) at a rate such that the reaction temperature is maintained at 25° to 30° C. Stir for 17 h at room temperature, then quench the reaction with 40% NaHSO$_3$ (50 g). Concentrate (40°–45° C./60 Torr) the resulting mixture to a residue, partition the residue in 50 mL CH$_2$Cl$_2$ and 150 mL H$_2$O and wash the organic layer with 2×50 mL H$_2$O. Dry over anhydrous Na$_2$SO$_4$ and concentrate in vacuo to a residue. Distill the residue (70° to 76° C./0.05 Torr) to afford the epoxide product (racemic). $^1$H NMR (CDCl$_3$) δ: 7.42 (dd, $^1$H, J=1.5 Hz); 7.24 (m, 2H), 7.10 (d, $^1$H, J=5 Hz); 3.85 (d, $^1$H, J=3 Hz); 3.72 (m, $^1$H); 2.80 (m, $^1$H); 2.56 (dd, $^1$H, J=6, 11 Hz); 2.42 (m, $^1$H); 1.86 (m, $^1$H).

Step (b):

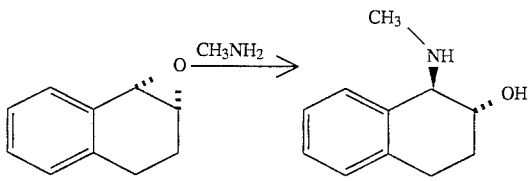

Charge a 120 mL Teflon® acid digestion bomb with the product of Step (a) (20.09 g, 0.1374 mol) and a stirring bar. Add liquid MeNH$_2$ (≈25 mL), seal the bomb and stir while heating at 100° C. for 22 h. Cool the bomb and then allow excess MeNH$_2$ to boil off. Distill the residue (kugelrohr at 160°–175° C./1 Torr) to afford the trans-amino alcohol product (racemic). $^1$H NMR (CDCl$_3$) δ: 7.30 (m, 4H); 3.86 (m, $^1$H); 3.64 (d, 1H, J=8 Hz); 2.89 (dd, 2H, J=5.4, 7.9 Hz); 2.42 (s, 3H); 2.25 (m, 3H); 1.86 (m, $^1$H).

Alternatively, the product of Step (a) is converted to the trans-amino alcohol product by treating with CH$_3$NH$_2$ via the procedure described in Crabb, et al., *Mag. Res. in Chem.*, 24, 798 (1986).

Step (c):

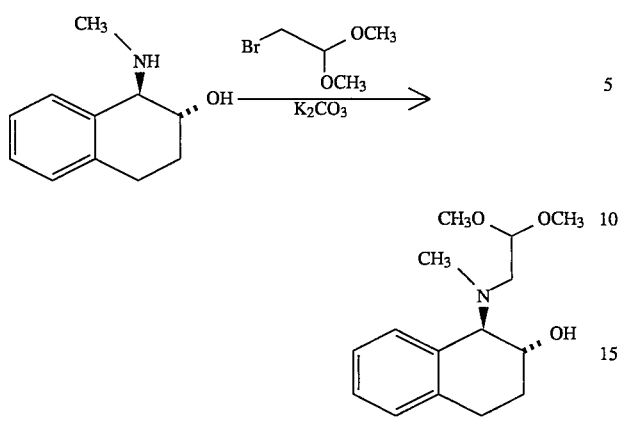

Combine the product of Step (b) (85.8 g, 0.484 mol), 484 mL anhydrous CH₃CN, K₂CO₃ (133.8 g, 0.968 mol) and bromoacetaldehyde dimethylacetal (123 g, 0.726 mol), and heat the mixture at reflux for 6 days. Cool to room temperature, decant the mixture and concentrate in vacuo to give a residue. Dissolve the residue in 350 mL of EtOAc and wash with 750 mL of water, then with 2× 160 mL of 2.5% HCl (aqueous). Combine the acidic washes, adjust to pH 8.8 by adding saturated Na₂CO₃ (aqueous) and extract with EtOAc. Wash the organic extract with brine, dry over MgSO₄ and concentrate in vacuo to give the product. ¹H NMR (CDCl₃) δ: 7.65 (d, 1 H, J=7.5 Hz); 7.05–7.30 (m, 3H); 4.65 (d, ¹H, J=11.3 Hz); 4.55 (br m, ¹H); 4.10 (br s, ¹H); 3.45 (s, 3H); 3.10 (s, 3H); 2.53–3.00 (m, 5H); 2.47 (s, 3H); 2.05 (m, ¹H); 1.61 (m, ¹H).

Step (d):

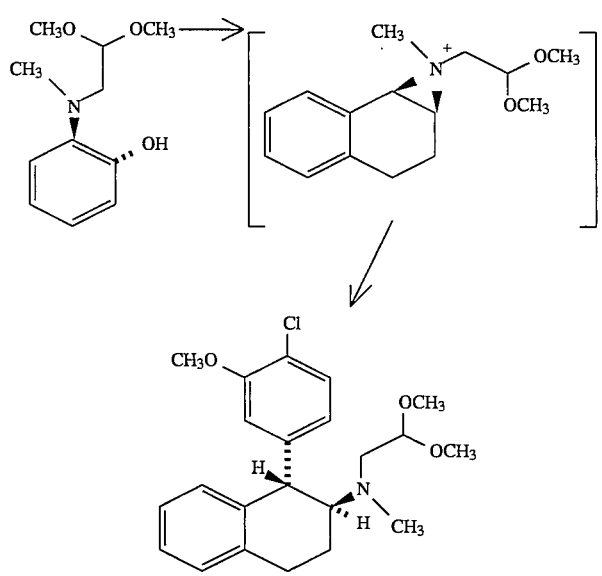

Combine the product of Step (c) (81.0 g, 0.305 mol), 1,10-phenanthroline (0.040 g, 0.222 mmol) and 305 mL anhydrous THF, cool the mixture to about 0° C., and add n-butyllithium (191 mL, 0.306 mmol, 1.6M solution in hexanes). Stir for 20 minutes, then add a solution of tosyl chloride (63.7 g, 0.334 mmol) in 200 mL of anhydrous THF. Stir the mixture for 1 h to form the aziridinium salt intermediate. Cool the mixture to about −30° C., then add the Grignard reagent from Preparation 1 (654 mL, 0.641 mmol, 0.98M in THF) and stir for 24 h at room temperature. Add 250 mL saturated NH₄Cl (aqueous), filter, then concentrate the filtrate in vacuo to a residue. Dissolve the residue in 230 mL of TBME, wash with 100 mL of water, then with 5% HCl (aqueous) (1×200 mL and 3×100 mL). Combine the acidic washes and extract with 230 mL of TBME. Adjust the acidic washes to pH 4.9 by adding saturated Na₂CO₃ (aqueous) and extract with 300 mL of TBME. Wash the organic layer with brine, dry over Na₂SO₄ and concentrate in vacuo to yield the title compound (racemic). ¹H NMR spectra is identical to material prepared in Example 1.

EXAMPLE 3

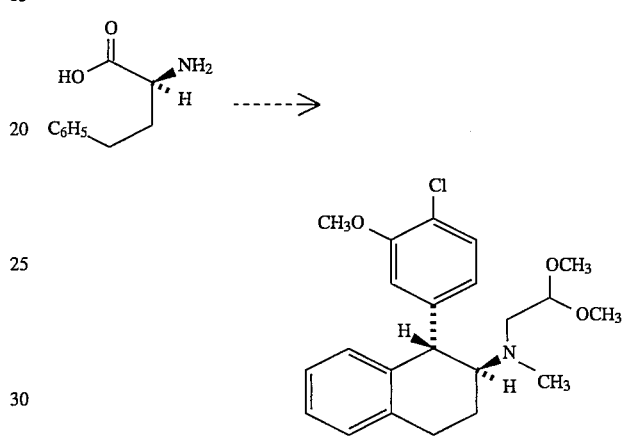

Step (a):

-continued

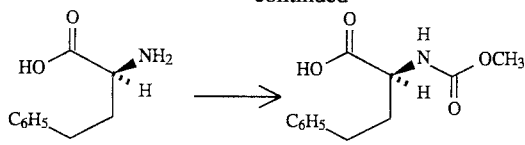

Combine (+)-α-aminobenzenebutanoic acid (100.14 g, 0.559 mol), NaOH (1.12 L, 1.12 mol, 1N aqueous solution) and Na$_2$CO$_3$ (88.61 g, 0.836 mol), and cool the mixture to about 0° C. Add methyl chloroformate (90 mL, 1.17 mol) dropwise over 15 min and stir at room temperature for 3 h. Add 500 mL 5% HCl then enough 50% HCl to bring to pH 2 (about 400 mL). Add 1 L of CH$_2$Cl$_2$, separate the layers, wash the aqueous layer with 3×150 mL CH$_2$Cl$_2$, then wash the combined organic layers with 1×250 mL brine. Dry over anhydrous MgSO$_4$ and concentrate in vacuo to yield the S-enantiomer of the carbamate product. $^1$H NMR (CDCl$_3$) δ: 7.10–7.30 (m, 5H); 5.25 (br d, $^1$H); 4.42 (br s, $^1$H); 3.70 (s, 3H); 2.70 (m, 2H); 2.20 (m, $^1$H) 2.01 (m, $^1$H).

Step (b):

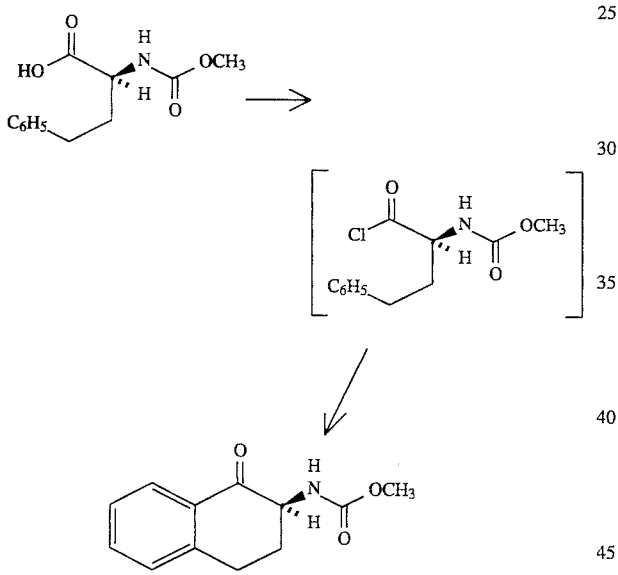

Combine the carbamate of Step (a) (124.9 g, 0.526 mol), 1 L of CH$_2$Cl$_2$ and SOCl$_2$ (39.0 mL, 0.535 mol) and heat the mixture to reflux for 3 h, then cool to room temperature to form a solution of the S-enantiomer of the acid chloride intermediate. Add the acid chloride solution dropwise to a mixture of AlCl$_3$ (211.22 g, 1.584 mol) and 750 mL CH$_2$Cl$_2$ over 2 h period, then stir for 1 h more. Add the reaction mixture gradually to 1 L of a saturated NH$_4$Cl/ice mixture. Filter the mixture and slurry the solids obtained in 1.5 L CH$_2$Cl$_2$ and 1 L water overnight, filter, combine the filtrates and separate the layers. Wash the aqueous layer with 2×200 mL of CH$_2$Cl$_2$, then wash the combined organic layers with 1×250 mL of brine. Dry over anhydrous MgSO$_4$ and concentrate in vacuo to yield the S-enantiomer of the ketone product, mp 119°–121.5° C. $^1$H NMR (CDCl$_3$) δ: 8.01 (d, 1H, J=7.5Hz); 7.62 (t, 1H, J=7.5Hz); 7.22–7.35 (m, 2H); 5.90 (br s, $^1$H); 4.40–4.50 (m, $^1$H); 3.72 (s, 3H); 3.25 (dt, $^1$H, J=3.7, 11.2Hz); 3.02 (m, $^1$H, J=15Hz); 2.78 (br m, $^1$H); 1.95 (dd, $^1$H, J=3.7, 15 Hz).

Step (c):

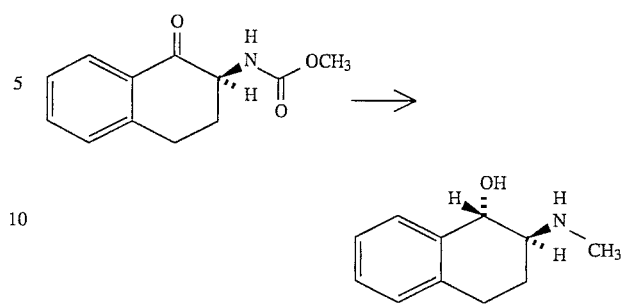

Combine the ketone of Step (b) (4.999 g, 22.802 mmol) and 50 mL anhydrous THF and cool to about 0° C. Add a solution of LiAlH$_4$ in Et$_2$O (46.0 mL, 46.0 mmol, 1M in Et$_2$O) gradually over 50 min, then heat at reflux for 2 h. Cool to about 0° C., then add 50 mL 5% HCl and 100 mL Et$_2$O and warm the mixture to room temperature. Filter, then wash solids with 25 mL water/10 mL 5% HCl, separate the layers and wash the organic layer with 1×20 mL 5% HCl. Combine the aqueous layers and add 15 mL saturated NaHCO$_3$, then add 100 mL EtOAc and separate the layers. Wash the aqueous layer with 3×50 mL EtOAc, dry the combined organic layers over anhydrous MgSO$_4$ and concentrate in vacuo to yield the trans-1S,2S-isomer of the amino alcohol product. $^1$H NMR (CDCl$_3$) δ7.68 (d, 1H, J=7.5Hz); 7.10–7.30 (m, 3H); 4.50 (d, $^1$H, J=7.5Hz); 2.90 (m, 2H); 2.67 (m, $^1$H); 2.55 (s, 3H); 2.27 (m, $^1$H); 2.00 (br s, 2H); 1.60 (m, $^1$H).

was also obtained. $^1$H NMR (CDCl$_3$) δ: 7.48 (m, $^1$H); 7.10–7.30 (m, 3H); 4.71 (d, $^1$H, J=3.8Hz); 2.75–3.00 (m, 3H); 2.55 (br s, 5H); 1.95 (m, $^1$H); 1.75 (m, $^1$H).

Step (d):

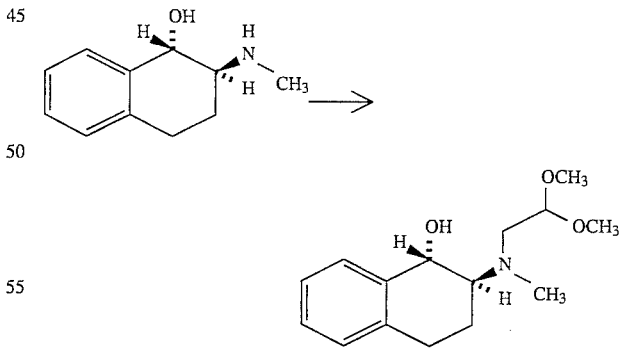

Combine the trans-amino alcohol of Step (c) (1.010 g, 5.698 mmol), 10 mL anhydrous CH$_3$CN and KF over alumina (3.050 g, 19.06 mmol) and stir for 5 min. Add bromo acetaldehyde dimethylacetal (1.4 mL, 11.8 mmol) and heat the mixture at reflux for 2 days. Cool to room temperature, add 25 mL EtOAc and filter though Celite®. Wash the solids with 10 mL EtOAc and 10 mL CH$_2$Cl$_2$, filter, then concentrate the combined filtrates in vacuo to yield the 1S,2S-isomer of the product. Purify by flash chromatography (silica gel, 30–100% EtOAc/hexanes and then to 60% MeOH saturated with ammonia/EtOAc). $^1$H NMR (CDCl$_3$) δ: 7.65 (d, $^1$H, J=7.5Hz); 7.05–7.30 (m, 3H); 4.65 (d, $^1$H, J=11.3Hz); 4.55 (br m, $^1$H); 4.10 (br s, $^1$H); 3.45 (s, 3H); 3.10 (s, 3H); 2.53–3.00 (m, 5H); 2.47 (s, 3H); 2.05 (m, $^1$H); 1.61 (m, $^1$H).

Step (e):

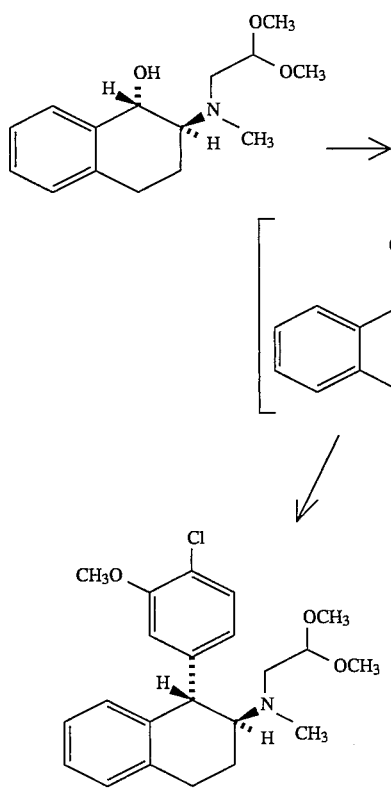

Combine the product of Step (d) (633.3 mg, 2.3867 mmol) and 2 mL THF and cool to about 0° C. Add a solution of n-butyllithium (1.20 mL, 2.45 mmol, 2.04M in hexane), stir for 10 min, then add tosyl chloride (456.4 mg, 2.3939 mmol) and stir for 15 min more to form the aziridinium salt intermediate. Add a solution of the Grignard reagent of Preparation 1 (5.8 mL, 4.8 mmol, 0.83M in THF) and stir at room temperature for 17 h. Add 10 mL saturated NH$_4$Cl and 25 mL EtOAc, then filter and wash the solids with 10 mL EtOAc. Combine the filtrates, separate the layers, wash the organic layer with 1×10 mL of brine, dry over anhydrous MgSO$_4$ and concentrate in vacuo to a residue. Flash chromatograph (silica gel, 5% to 100% EtOAc/hexane) to yield the named compound. $^1$H NMR (CDCl$_3$) δ: 6.65–7.30 (m, 7H); 4.12 (t, $^1$H, J=5.6Hz); 4.09 (d, $^1$H, J=11.3Hz); 3.82 (s, 3H); 3.21 (s, 3H); 3.12 (s, 3H); 2.95 (m, 3H); 2.60 (dd, 2H, J=5.6, 11.3Hz); 2.31 (s, 3H); 2.08 (m, $^1$H); 1.70–1.80 (m, $^1$H).

EXAMPLE 4

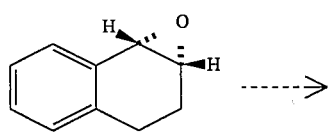

-continued

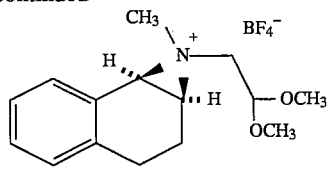

Step (a):

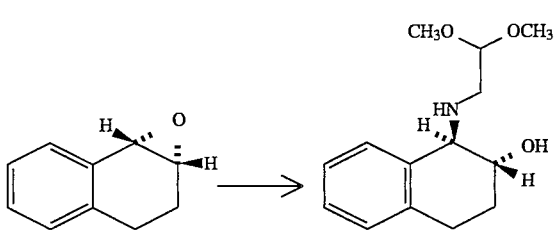

Charge a 30-mL Teflon® acid digestion bomb with the chiral epoxide (see Preparations 2 and 3) (1.00 g, 6.866 mmol) and amino acetaldehyde dimethyl acetal (2.171 g, 20.651 mmol). Seal and heat to 95° C. for 23 h. Cool and flash chromatograph (silica gel, 1% to 10% MeOH/CH$_2$Cl$_2$) to yield the amino alcohol product. $^1$H NMR (DMSO-d$_6$) δ: 7.38 (d, $^1$H, J=8Hz); 7.10 (m, 3H); 4.72 (d, $^1$H, J=2Hz); 4.42 (t, $^1$H, J=6.8Hz); 3.82 (m, $^1$H); 3.52 (d, 1H, J=7Hz); 3.42 (s, 3H); 3.40 (s, 3H); 2.73 (m, 3H); 2.54 (m, $^1$H); 2.00 (m, $^1$H); 1.78 (br s, $^1$H); 1.68 (m, H).

Step (b);

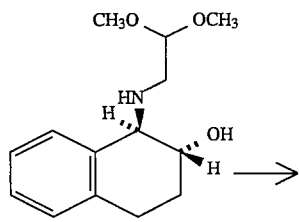

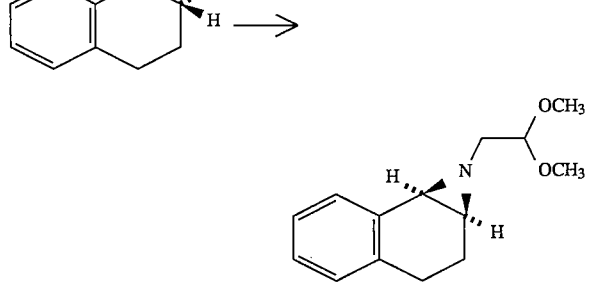

Combine the product of Step (a) (3.647 g, 14.512 mmol), 75 mL of CH$_3$CN and (C$_6$H$_5$)$_3$PBr$_2$ (9.472 g, 22.439 mmol) and cool to 0° C. Add a solution of Et$_3$N (6.50 mL, 46.600 mmol) in 5.5 mL CH$_3$CN dropwise over 10 min, stir for 90 min, then filter and concentrate. Slurry the filtrate with 20 mL n-hexane, filter and concentrate in vacuo to a residue. Flash chromatograph the residue (silica gel, 20–60% EtOAc/hexanes) to yield the aziridine product. $^1$H NMR (CDCl$_3$) δ: 7.10–7.35 (m, 4H); 4.51 (t, $^1$H, J=6.8Hz); 3.40 (2s, 6H); 2.65–2.87 (m, 2H); 2.42–2.55 (m, 3H); 2.21–2.31 (m, 2H); 1.53 (dd, $^1$H J=6.8, 11.3Hz).

The aziridine can also be formed by treating the product of Step (a) with mesyl chloride and Et$_3$N instead of (C$_6$H$_5$)$_3$PBr$_2$ and Et$_3$N.

Step (c):

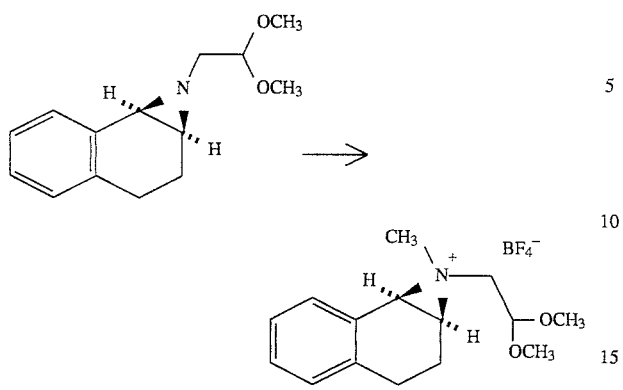

Combine the product of Step (b) (12.60 g, 51.30 mmol) and 200 mL dry $CH_2Cl_2$, and cool to $-20°$ C. Add purified $(CH_3)_3OBF_4$ (12.00 g, 81.00 mmol) and stir for 20 h at $-20°$ C. Filter off the excess $(CH_3)_3OBF_4$, while excluding moisture, then treat the filtrate with $Et_2O$ at $-20°$ C. Collect the resulting precipitate under argon, wash with cold $Et_2O$ and dry under vacuum at room temperature to give the chiral aziridinium tetrafluoroborate salt. $^1$H NMR ($CDCl_3$) δ: 7.60 (dd, $^1$H); 7.30 (m, 3H); 4.80 (t, $^1$H); 4.45 (d, $^1$H); 4.00 (m, 1H); 3.80 (dd, 1H); 3.50 (d, 6H); 3.35 (dd, $^1$H); 2.80–3.05 (m, $^1$H); 2.55–2.75 (m, 2H); 2.50 (s, 3H); 2.10–2.40 (m, $^1$H).

Purified $(CH_3)_3OBF_4$ is prepared from commercially available $(CH_3)_3OBF_4$ as follows. Slurry under argon in dry $CH_2Cl_2$ (two volumes) at 0° C. and stirred for 30 min. Filter the mixture under argon, wash with dry $CH_2Cl_2$, dry $Et_2O$ and then dry in vacuo at room temperature for 3 h. The solid is stored at 5° C. in a desiccator over $P_4O_{10}$ under argon.

EXAMPLE 5

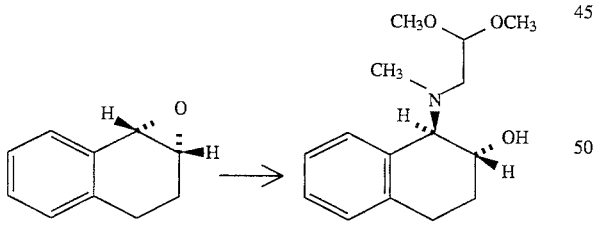

Charge a 30 mL Teflon® acid digestion bomb with the epoxide of Preparation 2 (or Preparation 3) (2.613 g, 17.872 mmol) and N-methylamino acetaldehyde dimethyl acetal (2.747 g, 23.055 mmol). Seal and heat to 95° C. for 20 h. Cool and flash chromatograph (silica gel, 2% to 5% MeOH/ $CH_2Cl_2$) to give the title compound. $^1$H NMR ($CDCl_3$)δ: =7.12 (m, 4H); 4.50 (t, $^1$H, J=7Hz); 4.13 (s, $^1$H); 3.72 (m, 2 H); 3.40 (s, 6H); 3.08 (d, 2H, J=7Hz); 3.86 (m, 2H); 2.48 (S, 3H); 2.22 (m, $^1$H); 80 (m, $^1$H).

EXAMPLE 6

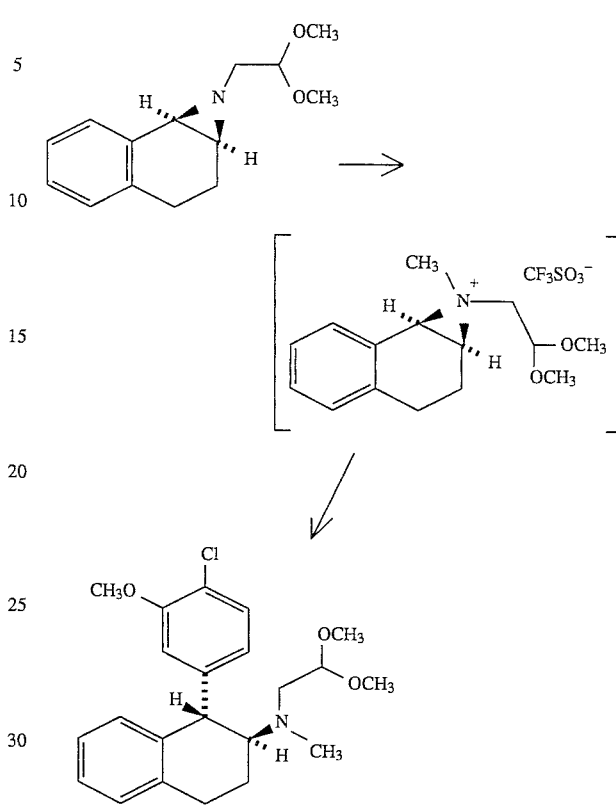

Combine the chiral aziridine of Example 4, Step (b) (0.50 g, 2.144 mmol) and 4 mL anhydrous THF. Add methyl triflate (0.363 g, 2.209 mmol), stir for 20 min, then add the Grignard reagent of Preparation 1 (1.50 mmol) and stir at room temperature for 17 h. Add 50 mL $H_2O$ and 50 mL EtOAc, separate, extract the aqueous layer with 1× 50 mL EtOAc, and wash the combined organic layers with 1×25 mL brine. Dry over anhydrous $MgSO_4$ and concentrate in vacuo to a residue. Flash chromatograph the residue (silica gel, 20–40% EtOAc/hexanes) to the title compound. $^1$H NMR was identical to the material prepared in Example 3.

EXAMPLE 7

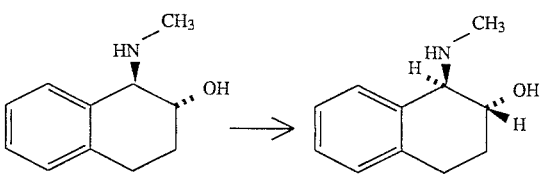

Combine the racemic amino alcohol from Example 2, Step (b) (160 g) and 1 L of MeOH. Add a hot solution of L-(+)-tartaric acid (68 g) in 300 mL of MeOH. Seed the mixture with a few crystals of the L-(+)tartrate salt of 1R,2R-isomer of the title compound and stir while cooling the mixture to $-5°$ C. Filter and wash the solid with cold MeOH to give the tartrate salt.

Dissolve the tartrate salt in hot MeOH and concentrate until crystals begin to form. Stir the resulting mixture while cooling to $-5°$ C. Filter and wash with cold MeOH to obtain the purified tartrate salt. m.p.=214°–216° C. $[α]_D^{20°\ c}$=+

28.1° (water). Elemental Analysis: calculated for $C_{26}H_{36}N_2O_8$—C, 61.92;H, 7.15; N, 5.55; found—C, 61.89;H, 7.12; N, 5.59.

Add the purified tartrate salt (61.33 g, 0.122 mol) to 10% $NH_{40}H$ (183 mL), then extract with TBME (3×250 mL). Combine the extracts, dry over $MgSO_4$ and concentrate in vacuo to give the chiral amino alcohol. $[\alpha]_D^{20 \ C}=+15.3°$ (MeOH). $^1H$ NMR using a chiral shift reagent of the formula

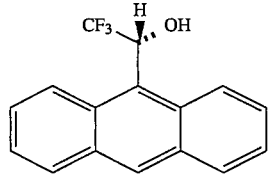

indicates >99% e.e. for the chiral amino alcohol.

We claim:
1. A process for preparing a compound of the formula

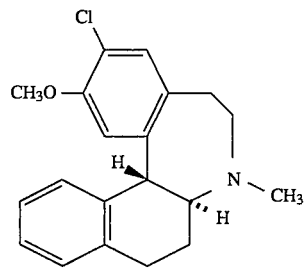

comprising:
(a) reacting an aziridinium salt of the formula

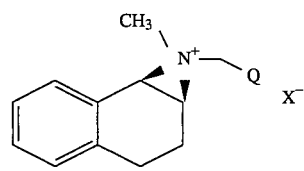

wherein: Q is a group of the formula

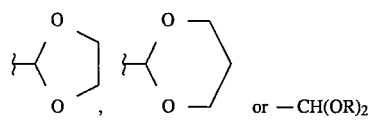

wherein R is $C_1$–$C_6$ alkyl; and $X^-$ is a counterion, with a reagent of the formula

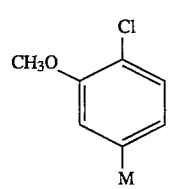

wherein M is selected from $MgL$, $ZnL$, $TiL_3$, $CeL_2$, $MnL$ or $CuL$, and L is a halide selected from Br, Cl or I; to form the compound of formula (IV); and
(b) cyclizing the compound of the formula (IV)

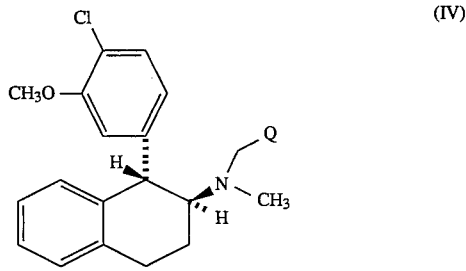

wherein: Q is a group of the formula

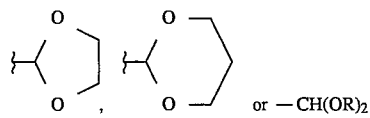

wherein R is $C_1$–$C_6$ alkyl; by treating with a strong acid followed by treatment with a hydride reducing agent.

2. A process of claim 1 wherein the aziridinium salt is prepared by a process comprising the steps:
(A1) epoxidizing 1,2-dihydronaphthalene to form an epoxide of the formula

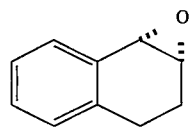

as a racemate by reacting with:
(i) $H_2O_2$ in the presence of a base; or
as predominantly one enantiomer by reacting with:
(ii) NaOCl in the presence of Mn(III) salen catalyst; or
(iii) $OsO_4$ in the presence of NMMO and dihydroquinine 4-chlorobenzoate, followed by treating the resulting cis diol with $(C_6H_5)_3PBr_2$ in the presence of a tertiary amine base;
(A2) regioselectively reacting the epoxide of step (A1) with methylamine to form an aminoalcohol of the formula

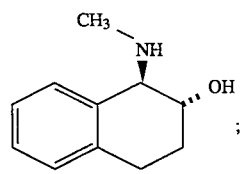

(A3) N-alkylating the aminoalcohol of step (A2) with a compound of the formula J—$CH_2$—Q, wherein J is a leaving group, and Q is as defined above; and
(A4) cyclizing the product of step (A3) by treating with an alkyllithium reagent and a sulfonyl chloride; to form the aziridinium salt.

3. A process of claim 1 wherein the aziridinium salt is prepared in optically active form by a process comprising the steps:
(B1) reacting S-(+)-2-amino-4-phenylbutanoic acid with ClCO₂R² to form a carbamate of the formula

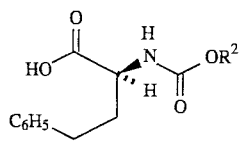

wherein R² is benzyl or C₁–C₆ alkyl;

(B2) reacting the carbamate of step (B1) with a chlorinating agent, then cyclizing the resulting acid chloride by treating with a Lewis acid to form a ketone of the formula

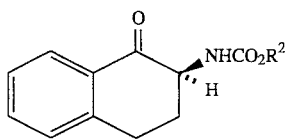

wherein R² is as defined above;

(B3) reducing the ketone of step (B2) by reacting with a hydride reducing agent to form a compound of the formula

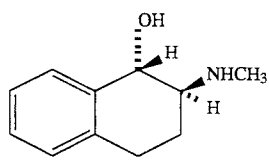

(B4) N-alkylating the product of step (B3) by reacting with a compound of the formula J—CH₂—Q, wherein J is a leaving group and Q is as defined above; and (B5) cyclizing the product of step (B4) by treating with an alkyllithium reagent and a sulfonyl chloride; to form the aziridinium salt.

4. A process of claim 1 wherein the aziridinium salt is prepared by a process comprising the steps:

(C1) converting 1,2-dihydronaphthalene to an epoxide of the formula

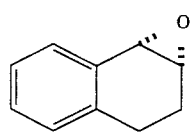

by the process of step (A1);

(C2) reacting the epoxide of step (C1) with an amine of the formula HN(R¹)—CH²—Q, wherein R¹ is H or CH₃, and Q is as defined above, to form an amino alcohol of the formula

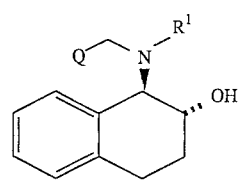

(C3)
(I) where R¹ is H, cyclizing the product of step (C2) to form an aziridine of the formula

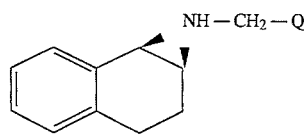

by reacting with:
(i) (C₆H₅)₃PBr₂; or
(ii) mesyl chloride or tosyl chloride, in the presence of a tertiary amine base;
followed by N-methylating the resulting aziridine by treating with:
(iii) CF₃SO₃CH₃; or
(iv) (CH₃)₃OBF₄;
to form the aziridinium salt; or
(II) where R¹ is CH₃, cyclizing the product of step (C2) by treating with an alkyllithium reagent and a sulfonyl chloride;
to form the aziridinium salt.

5. A process of claim 1 wherein the aziridinium salt is prepared in optically active form by a process comprising the steps:

(D1) resolving a trans-amine of the formula

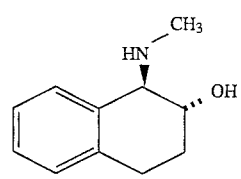

by treating with L-(+)-tartaric acid in an alcohol solvent to form the tartrate salt, recrystallizing the tartrate salt from an alcohol solvent, then treating the tartrate salt with base to form a chiral amine of the formula

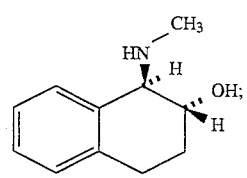

(D2) N-alkylating the chiral amine of step (D1) by reacting with a compound of the formula J—CH₂—Q, wherein J is a leaving group and Q is as defined above, in the presence of a base to form a compound of the formula

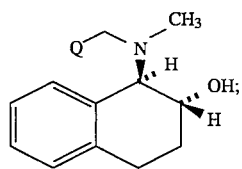

(D3) cyclizing the product of step (D2) by treating with an alkyllithium reagent and a sulfonyl chloride; to form the aziridinium salt.

6. A process of claim 1 wherein M is MgBr and the cyclization of compound (IV) is effected by treating with a strong acid followed by treatment with a hydride reducing agent.

7. A process of claim 6 wherein: Q is —CH(OCH$_3$)$_2$; the counterion X$^-$ is Cl$^-$, BF$_4^-$, CH$_3$C$_6$H$_4$SO$_3^-$, C$_6$H$_5$SO$_3^-$, CH$_3$SO$_3^-$ or CF$_3$SO$_3^-$; the strong acid is CH$_3$SO$_3$H; and the hydride reducing agent is BH$_3$.tBuNH$_2$ or NaBH$_4$.

8. A process of claim 2 wherein: the base of step (A1)(i) is NaHCO$_3$ or KHCO$_3$; the tertiary amine base of Step (A1)(iii) is Et$_3$N; J is Br; the alkyllithium reagent of Step (A4) is n-butyllithium; and the sulfonyl chloride of Step (A4) is tosyl chloride, nosyl chloride, brosyl chloride, benzene sulfonyl chloride or mesyl chloride.

9. A process of claim 3 wherein: the chlorinating agent of step (B2) is oxalyl chloride or SOCl$_2$; the Lewis acid of step (B2) is AlCl$_3$; the hydride reducing agent of step (B3) is LiAlH$_4$; J is Br; the alkyllithium reagent of Step (B5) is n-butyllithium; and the sulfonyl chloride of Step (B5) is tosyl chloride, nosyl chloride, brosyl chloride, benzene sulfonyl chloride or mesyl chloride.

10. A process of claim 4 wherein: the tertiary amine base of step (C3)(ii) is Et$_3$N; the alkyllithium reagent of Step (C3)(II) is n-butyllithium; and the sulfonyl chloride of Step (C3)(II) is tosyl chloride, nosyl chloride, brosyl chloride, benzene sulfonyl chloride or mesyl chloride.

11. A process of claim 5 wherein: the alcohol solvent of step (D1) is methanol; the base of step (D1) is NH$_4$OH, Na$_2$CO$_3$ or K$_2$CO$_3$; J is Br; the alkyllithium of step (D3) is n-butyllithium; and the sulfonyl chloride of Step (D3) is tosyl chloride, nosyl chloride, brosyl chloride, benzene sulfonyl chloride or mesyl chloride.

12. A compound of the formula

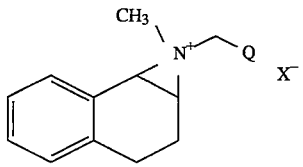

wherein: X$^-$ is halide, BF$_4^-$ or R$^3$SO$_3^-$, wherein R$^3$ is C$_1$–C$_6$ alkyl, CF$_3$, benzyl, phenyl or Z-substituted phenyl, wherein Z is C$_1$–C$_6$ alkyl, nitro or bromo; and Q is a group of the formula

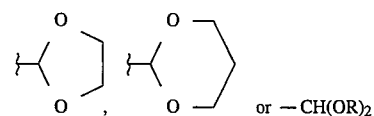 or —CH(OR)$_2$ wherein R is C$_1$–C$_6$ alkyl.

13. A compound of claim 12 having the absolute stereochemistry as shown in the formula

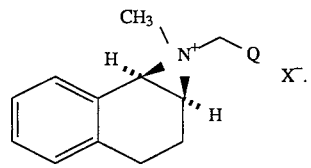

* * * * *